United States Patent
Arba-Mosquera

(10) Patent No.: US 12,220,353 B2
(45) Date of Patent: Feb. 11, 2025

(54) METHOD FOR CONTROLLING AN EYE SURGICAL LASER AND TREATMENT DEVICE

(71) Applicant: SCHWIND EYE-TECH-SOLUTIONS GMBH, Kleinostheim (DE)

(72) Inventor: Samuel Arba-Mosquera, Aschaffenburg (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 0 days.

(21) Appl. No.: 16/995,371

(22) Filed: Aug. 17, 2020

(65) Prior Publication Data
US 2021/0052424 A1 Feb. 25, 2021

(30) Foreign Application Priority Data
Aug. 19, 2019 (DE) .................... 10 2019 122 166.8

(51) Int. Cl.
*A61F 9/008* (2006.01)
*A61B 17/00* (2006.01)

(52) U.S. Cl.
CPC ............. *A61F 9/00825* (2013.01); *A61B 2017/00154* (2013.01); *A61F 2009/00844* (2013.01);
(Continued)

(58) Field of Classification Search
CPC ........ A61F 9/00825; A61F 2009/00844; A61F 2009/00872; A61F 2009/00897; A61B 2017/00154
See application file for complete search history.

(56) References Cited

U.S. PATENT DOCUMENTS

| | | | | |
|---|---|---|---|---|
| 5,993,438 A | * | 11/1999 | Juhasz | A61F 9/008 606/5 |
| 6,099,521 A | * | 8/2000 | Shadduck | A61F 9/00802 606/4 |

(Continued)

FOREIGN PATENT DOCUMENTS

| | | |
|---|---|---|
| CA | 2 620 295 A1 | 4/2007 |
| DE | 10 2005 049 281 A1 | 4/2007 |

(Continued)

OTHER PUBLICATIONS

German Office Action issued Apr. 27, 2020 in corresponding German Patent Application No. 10 2019 122 166.8.
(Continued)

*Primary Examiner* — Lynsey C Eiseman
*Assistant Examiner* — Skylar Lindsey Christianson
(74) *Attorney, Agent, or Firm* — MEDLER FERRO WOODHOUSE & MILLS PLLC

(57) ABSTRACT

A method is disclosed for controlling an eye surgical laser for the separation of a volume body from a cornea by using a control device such that the laser emits pulsed laser pulses in a shot sequence in a predefined pattern into the cornea. Interfaces of the volume body to be separated are defined by the predefined pattern and the interfaces are created by a plurality of cavitation bubbles generated by photodisruption. The plurality of cavitation bubbles is generated along at least one cavitation bubble path and the control device controls the shot sequence of the laser for generating a preset smoothness value such that a common overlap area of the cavitation bubbles is generated at least between adjacent cavitation bubbles located on the same cavitation bubble path depending on a geometry of the respective cavitation bubble.

15 Claims, 2 Drawing Sheets

(52) U.S. Cl.
CPC ............... *A61F 2009/00872* (2013.01); *A61F 2009/00897* (2013.01)

(56) References Cited

U.S. PATENT DOCUMENTS

| | | |
|---|---|---|
| 2005/0165387 A1 | 7/2005 | Lubatschowski et al. |
| 2007/0010804 A1* | 1/2007 | Rathjen ................... A61F 9/008 606/5 |
| 2008/0319464 A1 | 12/2008 | Bischoff et al. |
| 2009/0149841 A1* | 6/2009 | Kurtz ..................... A61B 18/20 606/4 |
| 2010/0331831 A1* | 12/2010 | Bischoff ............. A61F 9/00836 606/5 |
| 2015/0032091 A1* | 1/2015 | Teuma ................. A61F 9/0084 606/5 |
| 2017/0340483 A1* | 11/2017 | Rill ......................... A61B 3/13 |
| 2019/0015250 A1 | 1/2019 | Rathjen |

FOREIGN PATENT DOCUMENTS

| | | |
|---|---|---|
| DE | 10 2008 051 644 A1 | 4/2010 |
| EP | 3 427 705 A1 | 1/2019 |

OTHER PUBLICATIONS

Notification of the First Office Action issued Sep. 26, 2023 in CN Appl. No. 202010839904.9.

\* cited by examiner

METHOD FOR CONTROLLING AN EYE SURGICAL LASER AND TREATMENT DEVICE

FIELD

The invention relates to a method for controlling an eye surgical laser for the separation of a volume body with a predefined posterior interface and a predefined anterior interface from a human or animal cornea. Further, the invention relates to a treatment device with at least one surgical laser for the separation of a volume body with predefined interfaces of a human or animal eye by means of photodisruption and with at least one control device for the laser or lasers. Furthermore, the invention relates to a computer program as well as to a computer-readable medium.

BACKGROUND

Opacities and scars within the cornea, which can arise by inflammations, injuries or native diseases, impair the sight. In particular in case that these pathological and/or unnaturally altered areas of the cornea are located in the axis of vision of the eye, clear sight is considerably disturbed. In known manner, the thus altered areas are eliminated by so-called phototherapeutic keratectomy (PTK) by means of an ablatively effective laser, for example an excimer laser. However, this is only possible if the pathological and/or unnaturally altered areas of the cornea are located in the superficial layers of the cornea. Subjacent areas, in particular within the stroma, are not reachable by means of ablative laser methods. Here, additional measures such as for example the exposure of the subjacent areas have to be taken by means of an additional corneal incision. By the additional measures, the treatment duration is disadvantageously considerably increased. In addition, there is the risk that further complications such as for example the occurrence of inflammations at the incision locations occur by the additional corneal incisions.

BRIEF SUMMARY

Therefore, it is the object of the present invention to provide a method and a treatment device for controlling an eye surgical laser for the separation of a volume body with a predefined posterior interface and a predefined anterior interface from a human or animal cornea, by which the disadvantages of the prior art are overcome.

This object is solved by a method, a treatment device, a computer program as well as a computer-readable medium according to the independent claims. Advantageous configurations with convenient developments of the invention are specified in the respective dependent claims, wherein advantageous configurations of the method are to be regarded as advantageous configurations of the treatment device, of the computer program and of the computer-readable medium and vice versa.

An aspect of the invention relates to a method for controlling an eye surgical laser for the separation of a volume body with a predefined posterior interface and a predefined anterior interface from a human or animal cornea, wherein the method includes controlling the laser by means of a control device such that it emits pulsed laser pulses in a shot sequence in a predefined pattern into the cornea, wherein the interfaces of the volume body to be separated are defined by the predefined pattern and the interfaces are generated by means of an interaction of the individual laser pulses with the cornea by the generation of a plurality of cavitation bubbles generated by photodisruption, wherein the plurality of cavitation bubbles is generated along at least one cavitation bubble path and the control device controls the shot sequence of the laser for generating a preset smoothness value such that a common overlap area of the cavitation bubbles is generated at least between adjacent cavitation bubbles located on the same cavitation bubble path depending on a geometry of the respective cavitation bubble.

Thereby, it is allowed that the smoothness of the "incision" for generating the volume body can be improved. The smoothness can also be referred to as so-called "smoothness". In particular, the treatment duration can thereby be considerably shortened, possible complications by the usually required additional corneal incisions are avoided. Thus, the smoothness in particular indicates the smoother the volume body is generated, the cleaner incision surfaces and cleaner incision edges are generated at the volume body. Thus, the smoothness value in particular describes how clean the incision edges and the incision surfaces of the volume body are generated. In particular, it can for example be provided the smoother the incision is to be, the greater the preset smoothness value is to be selected.

In particular, the smoothness can for example be referred to as the absence of roughness. The roughness can for example be specified in units of length, for example micrometers. Presently, it can for example be provided that the roughness can be between nanometers and several micrometers. The smaller the roughness, the better the smoothness. The roughness can for example be calculated as a root mean square value of the deviations or as a standard deviation of a profile. It is also possible that the roughness can also be considered as an average value of the absolute deviations.

Thus, a distance between a respective cavitation bubble is in particular generated depending on the geometry of a respective cavitation bubble such that the preset smoothness value is complied with in generating the volume body.

By the method according to the invention, it is then for example allowed to reliably remove pathological and/or unnaturally altered areas in the stroma of the cornea, that is in subjacent areas of the cornea, which is referred to as cornea. Basically, an additional exposure of the cornea by means of additional corneal incisions is not required.

In other words, it is in particular provided that the cavitation bubbles overlap and bridges do not arise between the cavitation bubbles, but the cavitation bubbles are as far apart from each other as a treatment can be faster performed and an unnecessary stress in the form of energy for the cornea is also prevented. By the overlap of the cavitation bubbles, thus, a confluent bubble with the preset smoothness or the preset smoothness value can be generated. Thereby, the volume body can be generated, which can then in turn be removed.

In addition, it can be provided that the laser is controlled such that at least one incision or at least one opening is generated in the cornea at a predefined angle and with a predefined geometry, wherein the incision or the opening intersects an interface of the volume body and is formed up to a surface of the cornea such that the volume body is removable from the cornea via the incision or the opening.

By the term "interfaces", it is also to be understood that the volume body can optionally be defined and separated by means of a single interface located in the cornea. By the method according to the invention, thus, phototherapeutic keratectomy methods can be performed in deep areas of the cornea, in particular of the cornea, in particular of the stroma, on the one hand. On the other hand, the treatment duration for the separation of the volume body is shortened, in addition, the energy input into the cornea of the patient is also significantly reduced.

Further preferably, it can be provided if the predefined pattern is defined based on one or more control datasets, wherein the control dataset or datasets include(s) control data for positioning and/or for focusing individual laser pulses in the cornea. The determination of the control datasets is known and they in particular result from for example topographic and/or tachymetric measurements of the cornea to be treated as well as the type, the position and the extent of the for example pathological and/or unnaturally altered area within the stroma of the cornea. In particular, the control datasets are generated at least by providing topographic and/or tachymetric and/or morphologic data of the untreated cornea and providing topographic and/or tachymetric and/or morphologic data of the pathological and/or unnaturally altered area to be removed within the cornea.

In an advantageous form of configuration, the control of the laser is effected such that a lenticular volume body is separated. In other words, the volume body can therein be lenticularly formed, whereby a simple removal via the mentioned incision or the mentioned opening is possible. In that the volume body to be separated is only described and defined by the interfaces and these interfaces enclose for example the pathological and/or unnaturally altered tissue or the corresponding altered area on the one hand and are generated by means of photodisruption on the other hand, a full-surface or full-volume ablation of the volume body can be omitted. Only the interfaces are generated by means of photodisruption such that the predefined volume body can subsequently be removed from the cornea.

It is further advantageous if the control of the laser is effected such that a preset, spatial overlapping area geometry of the overlap area is generated between the adjacent cavitation bubbles along the cavitation bubble path. In other words, it is provided that the individual cavitation bubbles have a preset distance to each other. By the preset distance of the cavitation bubbles among each other, the spatial overlap area geometry can be generated. Thereby, it is allowed that a fixedly preset distance is generated between the individual cavitation bubbles such that the smoothness value, which is preset, can be correspondingly complied with. Thereby, an improved method for controlling an eye surgical laser can be provided.

In a further advantageous form of configuration, the control of the laser is effected such that a spatial overlap area extension of the overlap area is generated within a preset tolerance range for the overlap area between the adjacent cavitation bubbles along the cavitation bubble path. In other words, it is provided that a preset tolerance range is generated for the overlap area. This tolerance range is in particular provided such that the preset smoothness value is achieved. However, the overlap areas can then be differently formed within the tolerance range. For example, a natural distribution of the overlap area extensions within the tolerance range can be acceptable. Thereby, it is allowed that later caused diffraction effects within the cornea can be avoided and the smoothness value can nevertheless be reliably achieved.

Further, it has proven advantageous if the control of the laser is effected such that successively shot laser pulses are generated depending on a noise signal such that the spatial overlap area geometry is generated within the tolerance range for the overlap area. Thereby, it is allowed in simple manner correspondingly not to use rigid structures depending on the noise signal such that the corresponding diffraction effects within the cornea are avoided.

In a further advantageous form of configuration, the control of the laser is effected such that a plurality of cavitation bubbles is generated along a plurality of cavitation bubble paths of the predefined pattern, wherein the overlap area is respectively generated between the respective cavitation bubble paths. Thus, it is in particular provided that the overlap area is respectively formed between the cavitation bubbles as well as between the individual cavitation bubble paths. Thereby, it is allowed that the volume body can be generated with the preset smoothness value. For example, with a preset distance of the cavitation bubbles, a consecutive cavitation bubble path can have a half distance laterally offset and be shifted parallel by root of three halves of the distance. Thus, it is allowed that the volume body can be generated with shortened treatment duration.

Further, it has proven advantageous if the control of the laser is effected such that a meandering cavitation bubble path or a spiral cavitation bubble path or a grid-like cavitation bubble path or an annular cavitation bubble path or a triangular cavitation bubble path or a helical cavitation bubble path is generated. Therein, the start of the photodisruption by the individual laser pulses can be effected in the center of the respective interface or also at the edge of the respective interface. Thereby, it is in particular allowed that different cavitation bubble paths can be generated by means of different shot sequences. Thus, the volume body can be highly flexibly generated.

It is also advantageous if the control of the laser is effected such that the geometry of the generated cavitation bubbles is preset as spherical and the control of the laser is effected such that the spherical geometry of the cavitation bubbles is taken into account in the determination of the overlap area and/or in the determination of a tolerance range for the overlap area. This in particular has the background in that a corresponding cavitation bubble can only be generated at a preset energy density value. If this energy density value is exceeded, the cavitation bubble is generated, which is in particular substantially spherical and seems like a flat ellipse trough the closed cornea. The radius of the cavitation bubble is in particular approximately proportional to the cubic root of the pulse energy. By the specification of the cavitation bubble as spherical, the overlap area can thus in particular be simply yet reliably determined such that the preset smoothness value can be complied with.

It is further advantageous if the control of the laser is effected such that a radius of the spherical geometry is substantially preset as proportional to the cubic root of a pulse energy of the respective laser pulse and the overlap area and/or the tolerance range for the overlap area are determined depending on the preset radius. Thereby, an improved determination of the overlap area is allowed. In particular, the overlap area can thereby be reliably determined such that the preset smoothness value can be complied with or achieved.

It is further advantageous if the control of the laser is effected such that topographic and/or tachymetric and/or morphologic data of the cornea are taken into account. Thus, topographic and/or tachymetric measurements of the cornea to be treated as well as of the type, the position and the extent of the for example pathological and/or unnaturally altered area within the stroma of the cornea can in particular be taken into account. In particular, control datasets are generated at least by providing topographic and/or tachymetric and/or morphologic data of the untreated cornea and providing topographic and/or tachymetric and/or morphologic data of the pathological and/or unnaturally altered area to be removed within the cornea.

According to a further advantageous form of configuration, the control of the laser is effected such that the laser emits laser pulses in a wavelength range between 300 nanometers and 1400 nanometers, in particular between 700 nanometers and 1200 nanometers, at a respective pulse duration between 1 fs and 1 ns, in particular between 10 fs and 10 ps, and a repetition frequency of greater than 10 kHz, in particular between 100 kHz and 100 MHz. Such lasers are already used for photodisruptive methods in the eye surgery. The produced lenticule is subsequently removed via the incision in the cornea. However, the use of such photodisruptive lasers instead of ablatively acting lasers in the phototherapeutic keratectomy PTK is new and not known from the prior art. The use of photodisruptive lasers in the method according to the invention additionally has the advantage that the irradiation of the cornea is not to be effected in a wavelength range below 300 nm. This range is subsumed by the term "deep ultraviolet" in the laser technology. Thereby, it is advantageously avoided that an unintended damage to the cornea is effected by this very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is ensured.

A further aspect of the invention relates to a treatment device with at least one surgical laser for the separation of a volume body with predefined interfaces of a human or animal eye by means of photodisruption and with at least one control device for the laser or lasers, which is formed to execute the steps of the method according to the preceding aspect. The treatment device according to the invention allows that disadvantages occurring in the use of usual ablative treatment devices, namely relatively long treatment times and relatively high energy input by the laser into the cornea, are reliably avoided. These advantages are in particular achieved by the formation of the eye surgical laser as a photodisruptive laser.

Therein, the laser is suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz.

In an advantageous form of configuration of the treatment device, the treatment device comprises a storage device for at least temporary storage of at least one control dataset, wherein the control dataset or datasets include(s) control data for positioning and/or focusing individual laser pulses in the cornea, and includes at least one beam device for beam guidance and/or beam shaping and/or beam deflection and/or beam focusing of a laser beam of the laser. Therein, the mentioned control datasets are usually generated based on a measured topography and/or tachymetry and/or morphology of the cornea to be treated and the type of the pathologically and/or unnaturally altered area to be removed within the cornea.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including instructions, which cause the treatment device according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and the second inventive aspect, wherein advantageous configurations of each inventive aspect are to be regarded as advantageous configurations of the respectively other inventive aspect.

BRIEF DESCRIPTION OF THE FIGURES

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

DETAILED DESCRIPTION

Figure 1:
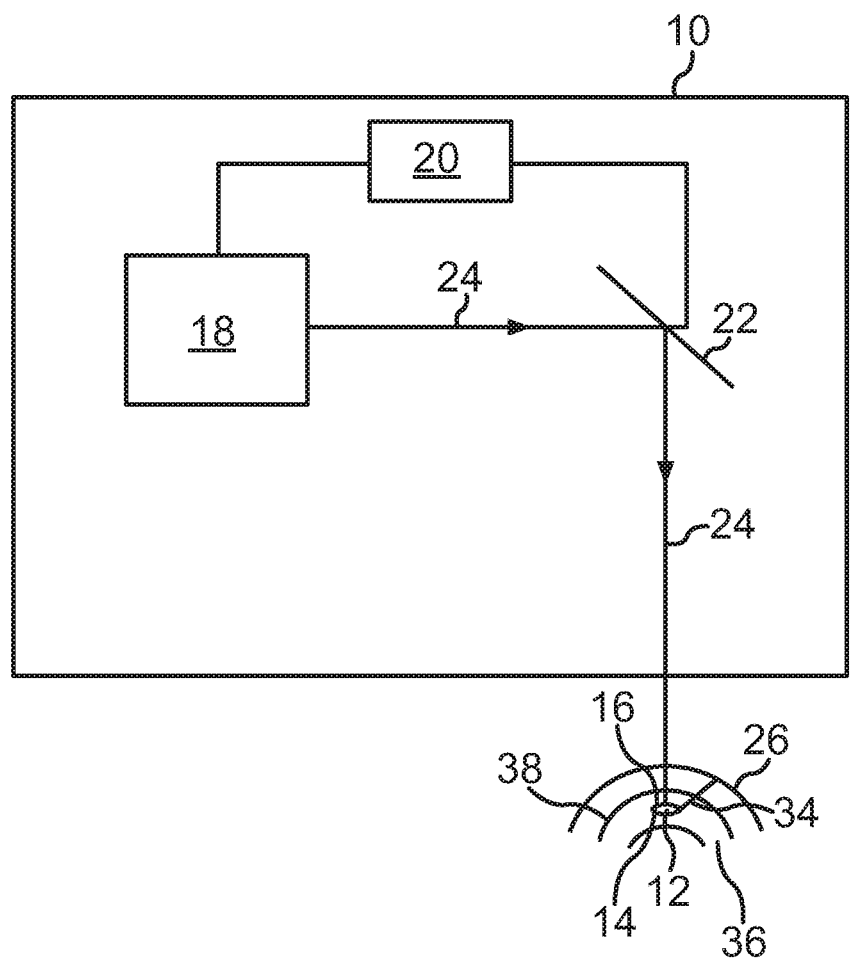
FIG. 1 is a schematic representation of a treatment device according to the invention.

FIG. 1 shows a schematic representation of a treatment device 10 with an eye surgical laser 18 for the separation of a predefined corneal volume or volume body 12 with predefined interfaces 14, 16 of a cornea of a human or animal eye by means of photodisruption. One recognizes that a control device 20 for the laser 18 is formed besides the laser 18, such that it emits pulsed laser pulses in a predefined pattern into the cornea, wherein the interfaces 14, 16 of the volume body 12 to be separated are generated by the predefined pattern by means of photodisruption. In the illustrated embodiment, the interfaces 14, 16 form a lenticular volume body 12, wherein the position of the volume body 12 is selected in this embodiment such that a pathological and/or unnaturally altered area 32 (see FIG. 2) within a stroma 36 of the cornea is enclosed. Furthermore, it is apparent from FIG. 1 that the so-called Bowman's membrane 38 is formed between the stroma 36 and an epithelium 28.

Furthermore, one recognizes that the laser beam 24 generated by the laser 18 is deflected towards a surface 26 of the cornea by means of a beam device 22, namely a beam deflection device such as for example a scanner. The beam deflection device 22 is also controlled by the control device 20 to generate the mentioned predefined pattern in the cornea.

The illustrated laser 18 is a photodisruptive laser, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 KHz, preferably between 100 kHz and 100 MHz.

In addition, the control device 20 comprises a storage device (not illustrated) for at least temporary storage of at least one control dataset, wherein the control dataset or datasets include(s) control data for positioning and/or for focusing individual laser pulses in the cornea. The position data and/or focusing data of the individual laser pulses are generated based on a previously measured topography and/or pachymetry and/or the morphology of the cornea and the pathological and/or unnaturally altered area 32 for example to be removed within the stroma 36 of the eye.

Figure 2:
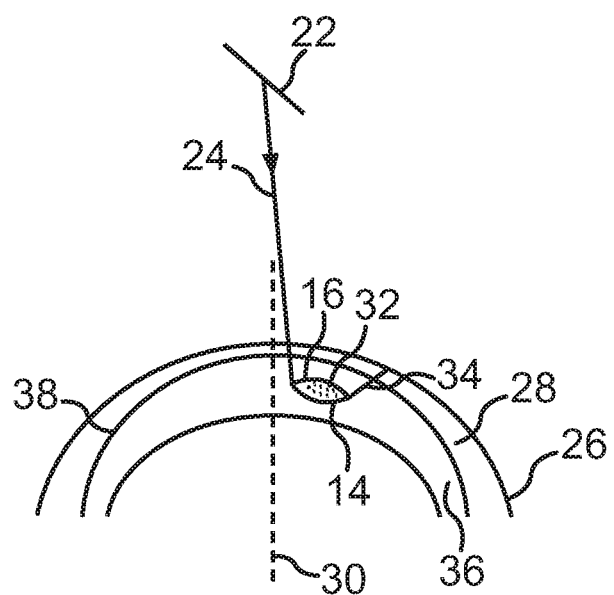
FIG. 2 is a schematic diagram of the generation of a volume body to be separated.

FIG. 2 shows a schematic diagram of the generation of the volume body 12 to be separated according to an embodiment of the present method. One recognizes that the interfaces 14, 16 are generated by means of the pulsed laser beam 24, which is directed towards the cornea or towards the surface 26 of the cornea via the beam deflection device 22. Therein, the interfaces 14, 16 form a lenticular volume body 12, which for example encloses the pathological and/or unnaturally altered area 22 within the stroma 36. Furthermore, the laser 18 generates a further incision 34 in the illustrated embodiment, which intersects the volume body 12 at a predefined angle and with a predefined geometry and is formed up to the surface 26 of the cornea. The volume body 12 defined by the interfaces 14, 16 can then be removed from the cornea via the incision 34. In the illustrated embodiment, the pathological and/or unnaturally altered area 32 is formed within the stroma 36 and outside of an optical axis 30 of the eye.

In the illustrated embodiment, the interface 14, that is the interface located deeper in the eye or the stroma 36, is first formed by means of the laser beam 24, wherein it then corresponds to the posterior interface 14. This can be effected by at least partially circularly and/or spirally guiding the laser beam 24 according to the predefined pattern. Subsequently, the interface 16 is generated in comparable manner, which then corresponds to the anterior interface 16 such that the interfaces 14, 16 form the lenticular volume body 12 (see also FIG. 1). Subsequently, the incision 34 is also generated by the laser 18. However, the order of the generation of the interfaces 14, 16 and of the incision 34 can also be changed.

Figure 3:
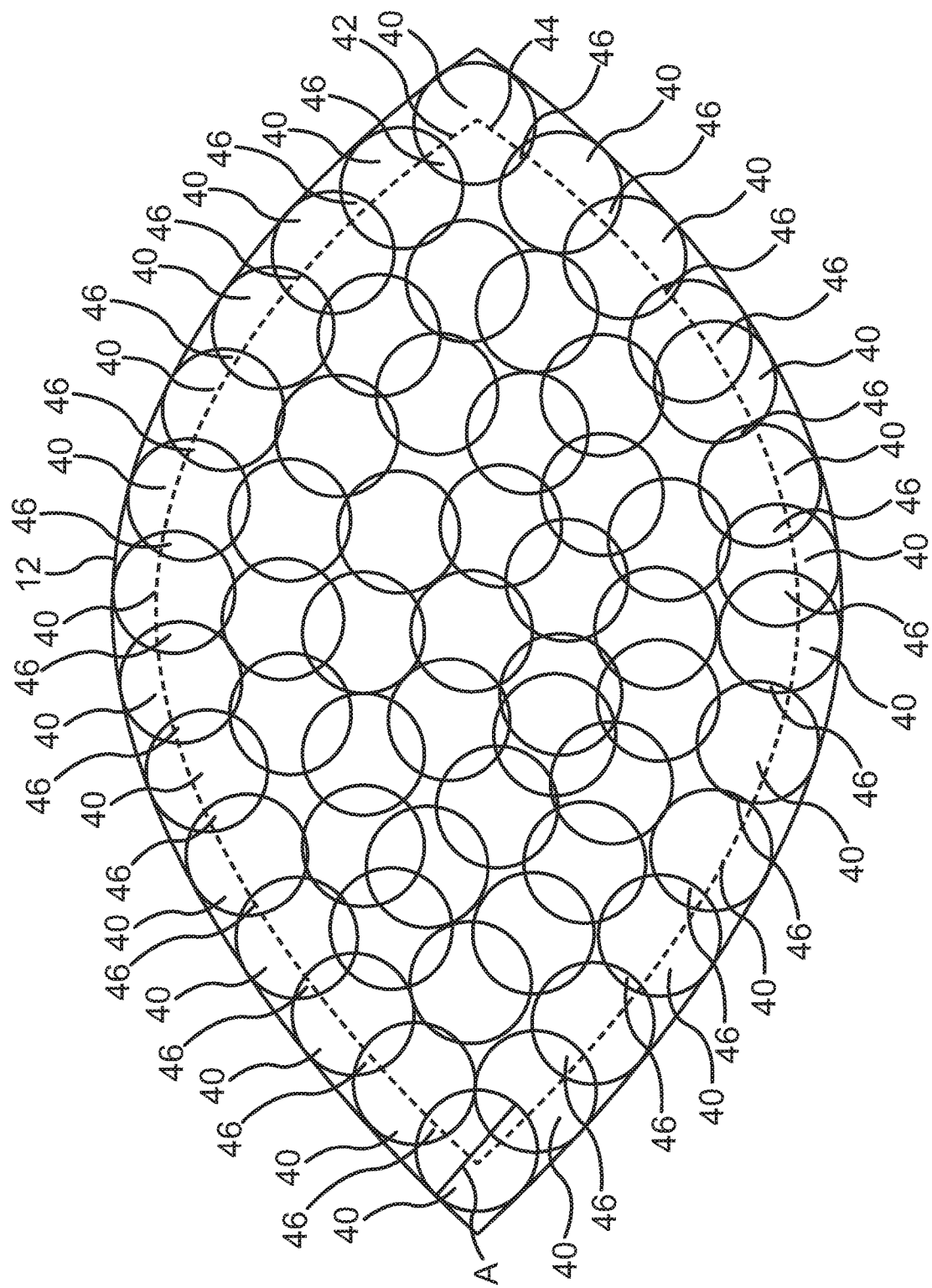
FIG. 3 is a schematic top view to a volume body.

FIG. 3 purely exemplarily shows a volume body 12 in a schematic top view. In particular, FIG. 3 shows that for controlling the laser 18 by means of the control device 20, the laser 18 is controlled such that it emits pulsed laser pulses in the predefined pattern into the cornea, wherein the interfaces 14, 16 of the volume body 12 to be separated are defined by the predefined pattern and the interfaces 14, 16 are generated by means of an interaction of the individual laser pulses with the cornea by the generation of a plurality of cavitation bubbles 40 generated by photodisruption along at least one cavitation bubble path 42, 44 and the control device 20 controls the shot sequence of the laser 18 for generating a preset smoothness value such that a common overlap area 46 of the cavitation bubbles 40 is generated at least between adjacent cavitation bubbles 40 located on the same cavitation bubble path 42, 44 depending on a geometry of the respective cavitation bubble 40.

In particular, FIG. 3 shows that the control of the laser 18 is effected such that a preset, spatial overlap area geometry of the overlap area 46 is generated between the adjacent cavitation bubbles 40 along the cavitation bubble path 42, 44, in particular along a first cavitation bubble path 42 in the present embodiment. In other words, the cavitation bubbles 40 have the preset, spatial overlap area along the first cavitation bubble path 42. It is in particular determined such that the preset smoothness value can be complied with. For example, it can be provided that a cavitation bubble 40 has a diameter A, wherein a corresponding overlap area is then selected such that the distances between the adjacent cavitation bubbles 40 correspond to $$\frac{A}{3^{0.25}}.$$

Further, FIG. 3 shows that the control of the laser 18 is effected such that a spatial overlap area geometry of the overlap area 46 is generated within a preset tolerance range for the overlap area 46 between the adjacent cavitation bubbles 40 along the cavitation bubble path 42, 44, in particular along a second cavitation bubble path 44 in the present embodiment. Hereto, it can for example be provided that the control of the laser 18 is effected such that successively shot laser pulses are generated depending on a noise signal such that the spatial overlap area geometry is generated within the tolerance range for the overlap area 46. In particular, diffraction effects arising afterwards can thereby be prevented from arising within the cornea. In particular, the tolerance range is selected such that the preset smoothness value is complied with or generated.

Further, it can in particular be provided that the control of the laser 18 is effected such that a plurality of cavitation bubbles 40 is generated along a plurality of cavitation bubble paths 42, 44 of the predefined pattern, wherein the overlap area 46 is respectively generated between the respective cavitation bubble paths 42, 44. Hereto, it can for example be provided that a distance is complied with between the cavitation bubble paths 42, 44, which corresponds to $$\left(\frac{A}{3^{0.25}}\right)\frac{3^{0.5}}{2}$$

or corresponds to $$A * \frac{3^{0.25}}{2}.$$

Further, the distance in a z-direction from one round to the next round can for example be determined by the formula:

$$\left(A * \frac{3^{0.25}}{2}\right)\frac{3^{0.5}}{4} \text{ or } A * \left(\frac{3^{0.75}}{8}\right)$$

In particular, it can further be provided that the control of the laser 18 is effected such that a meandering cavitation bubble path 42, 44 or a spiral cavitation bubble path 42, 44 or a grid-like cavitation bubble path 42, 44 or an annular cavitation bubble path 42, 44 or a triangular cavitation bubble path 42, 44 or a helical cavitation bubble path 42, 44 is generated.

Overall, the FIG. 3 further shows that the control of the laser 18 is effected such that the geometry of the generated cavitation bubbles 40 is specified as spherical and the control of the laser 18 is effected such that the spherical geometry of the cavitation bubbles 40 is taken into account in the determination of the overlap area 46 and/or in the determination of a tolerance range for the overlap area 46. Overall, it can hereto be provided that the control of the laser 18 is effected such that a radius, which can be determined by the diameter A in the present embodiment, of the spherical geometry is specified as being essentially proportional to the cubic root of a pulse energy of a respective laser pulse and the overlap area 46 and/or the tolerance range for the overlap area 46 are determined depending on the preset radius.

FIG. 3 in particular only shows an intermediate step such that it can in particular be provided that for generating the preset smoothness and for generating the volume body 12, respectively, still further cavitation bubbles 40 not illustrated are generated. For the sake of clarity, FIG. 3 is correspondingly illustrated, but it is not to be regarded as exhaustive.

What is claimed is:

1. A method for controlling an eye surgical laser for separation of a volume body with a predefined posterior interface and a predefined anterior interface from a human or animal cornea, comprising:
   controlling the laser using a control device such that the laser emits pulsed laser pulses in a shot sequence in a predefined pattern into the cornea,
   wherein the predefined posterior and anterior interfaces of the volume body to be separated are defined by the predefined pattern, and the predefined posterior and anterior interfaces are generated by an interaction of the pulsed laser pulses with the cornea that occurs due to a plurality of cavitation bubbles being generated by photodisruption,
   wherein the plurality of cavitation bubbles is generated along at least one cavitation bubble path and the control device controls the shot sequence of the laser for generating a preset smoothness value, wherein smoothness is related to an absence of roughness, and wherein the preset smoothness value is achieved by an overlap area being generated between adjacent cavitation bubbles located on the at least one cavitation bubble path,
   wherein, in order to achieve the preset smoothness value, a preset distance between adjacent cavitation bubbles and the overlap area to be generated between adjacent cavitation bubbles is determined based on a diameter (A) of a respective cavitation bubble of the plurality of cavitation bubbles, wherein the preset distance between adjacent cavitation bubbles corresponds to the formula $[A/(3^{0.25})]$, and
   wherein the control of the laser is effected such that a lenticular volume body is separated.

2. The method according to claim 1, wherein the control of the laser is effected such that a predetermined, spatial overlap area geometry of the overlap area is generated between the adjacent cavitation bubbles along the at least one cavitation bubble path.

3. The method according to claim 1, wherein the control of the laser is effected such that a spatial overlap area geometry of the overlap area is generated within a preset tolerance range for the overlap area between the adjacent cavitation bubbles along the at least one cavitation bubble path.

4. The method according to claim 1, wherein the control of the laser is effected such that the plurality of cavitation bubbles is generated along a plurality of cavitation bubble paths and wherein the overlap area is respectively generated between cavitation bubbles of adjacent cavitation bubble paths of the plurality of cavitation bubble paths.

5. The method according to claim 4, wherein the control of the laser is effected such that each of the plurality of cavitation bubble paths generated is a meandering cavitation bubble path or a spiral cavitation bubble path or a grid-like cavitation bubble path or an annular cavitation bubble path or a triangular cavitation bubble path or a helical cavitation bubble path.

6. The method according to claim 4, wherein a preset distance between adjacent cavitation bubble paths, in a z-direction, corresponds to the formula $[(A/8)*(3^{0.75})]$.

7. The method according to claim 1, wherein the control of the laser is effected such that a geometry of the generated cavitation bubbles is specified as spherical and the control of the laser is effected such that the spherical geometry of the cavitation bubbles is taken into account in the determination of the overlap area and/or in the determination of a tolerance range for the overlap area.

8. The method according to claim 7, wherein the control of the laser is effected such that a radius of the spherical geometry is specified as proportional to a cubic root of a pulse energy of a respective laser pulse and the overlap area and/or the tolerance range for the overlap area are determined depending on the specified radius.

9. The method according to claim 1, wherein the control of the laser is effected such that topographic and/or pachymetric and/or morphologic data of the cornea are taken into account.

10. The method according to claim 1, wherein the control of the laser is effected such that the laser emits laser pulses in a wavelength range between 300 nm and 1400 nm, at a respective pulse duration between 1 fs and 1 ns, and a repetition frequency of greater than 10 kHz.

11. The method according to claim 10, wherein the control of the laser is effected such that the laser emits laser pulses in a wavelength range between 700 nm and 1200 nm, at a respective pulse duration between 10 fs and 10 ps, and a repetition frequency of greater than 100 kHz and 10 MHz.

12. A treatment device with at least one surgical laser for the separation of a volume body with predefined interfaces of a human or animal eye using photodisruption and with at least one control device for the laser or lasers, the treatment device being configured to perform the method of claim 1.

13. The treatment device according to claim 12, wherein the control device comprises:
   at least one storage device for at least temporary storage of at least one control dataset, wherein the control dataset or datasets include(s) control data for positioning and/or for focusing individual laser pulses in the cornea; and
   at least one beam deflection device for beam guidance and/or beam shaping and/or beam deflection and/or beam focusing of a laser beam of the laser.

14. A non-transitory computer-readable medium storing instruction that, when executed by a processor, cause a treatment device with at least one laser for separation of a volume body with a predefined posterior interface and a predefined anterior interface of a human or animal cornea using photodisruption with at least one control device for controlling the laser to execute a method comprising:
- controlling the laser using a control device such that the laser emits pulsed laser pulses in a shot sequence in a predefined pattern into the cornea, wherein the predefined posterior and anterior interfaces of the volume body to be separated are defined by the predefined pattern and the predefined posterior and anterior interfaces are generated by an interaction of the pulsed laser pulses with the cornea that occurs due to a plurality of cavitation bubbles being generated by photodisruption,
- wherein the plurality of cavitation bubbles is generated along at least one cavitation bubble path and the control device controls the shot sequence of the laser for generating a preset smoothness value, wherein smoothness relates to an absence of roughness, and wherein the preset smoothness value is achieved by an overlap area being generated between adjacent cavitation bubbles located on the at least one cavitation bubble path,
- wherein, in order to achieve the preset smoothness value, a distance between adjacent cavitation bubbles and the overlap area to be generated between adjacent cavitation bubbles is determined based on a diameter (A) of a respective cavitation bubble of the plurality of cavitation bubbles, wherein the preset distance between adjacent cavitation bubbles corresponds to the formula $[A/(3^{0.25})]$, and
- wherein the control of the laser is effected such that a lenticular volume body is separated.

15. A method for controlling an eye surgical laser for separation of a volume body with a predefined posterior interface and a predefined anterior interface from a human or animal cornea, comprising:
- controlling the laser using a control device such that the laser emits pulsed laser pulses in a shot sequence in a predefined pattern into the cornea, wherein the control of the laser is effected such that topographic, pachymetric and morphologic data of the cornea are taken into account,
- wherein the predefined posterior and anterior interfaces of the volume body to be separated are defined by the predefined pattern, and the predefined posterior and anterior interfaces are generated by an interaction of the pulsed laser pulses with the cornea that occurs due to a plurality of cavitation bubbles being generated by photodisruption,
- wherein the plurality of cavitation bubbles is generated along at least one cavitation bubble path and the control device controls the shot sequence of the laser for generating a preset smoothness value, wherein smoothness is related to an absence of roughness, and wherein the preset smoothness value is achieved by an overlap area being generated between adjacent cavitation bubbles located on the at least one cavitation bubble path,
- wherein, in order to achieve the preset smoothness value, a preset distance between adjacent cavitation bubbles and the overlap area to be generated between adjacent cavitation bubbles is determined based on a diameter (A) of a respective cavitation bubble of the plurality of cavitation bubbles, wherein the preset distance between adjacent cavitation bubbles corresponds to the formula $[A/(3^{0.25})]$, and
- wherein the control of the laser is effected such that a lenticular volume body is separated.

* * * * *